United States Patent
Gassner et al.

(10) Patent No.: US 9,050,217 B2
(45) Date of Patent: Jun. 9, 2015

(54) INCONTINENCE ARTICLE IN PANT FORM

(71) Applicant: PAUL HARTMANN AG, Heidenheim (DE)

(72) Inventors: Oliver Gassner, Ulm (DE); Andreas Beyrle, Nattheim (DE)

(73) Assignee: PAUL HARTMANN AG, Heidenheim (DE)

( * ) Notice: Subject to any disclaimer, the term of this patent is extended or adjusted under 35 U.S.C. 154(b) by 143 days.

(21) Appl. No.: 13/896,571

(22) Filed: May 17, 2013

(65) Prior Publication Data

US 2013/0324962 A1  Dec. 5, 2013

Related U.S. Application Data

(60) Provisional application No. 61/659,438, filed on Jun. 14, 2012.

(30) Foreign Application Priority Data

May 18, 2012  (DE) .......................... 10 2012 208 392

(51) Int. Cl.
*A61F 13/49* (2006.01)
*A61F 13/496* (2006.01)
*A61F 13/15* (2006.01)
*A61F 13/58* (2006.01)

(52) U.S. Cl.
CPC ......... *A61F 13/49011* (2013.01); *A61F 13/496* (2013.01); *A61F 13/15593* (2013.01); *A61F 2013/49025* (2013.01); *A61F 2013/49038* (2013.01); *A61F 13/49017* (2013.01); *A61F 13/58* (2013.01)

(58) Field of Classification Search
CPC .......................... A61F 13/49019; A61F 13/539
See application file for complete search history.

(56) References Cited

U.S. PATENT DOCUMENTS

| | | | |
|---|---|---|---|
| 7,250,549 B2 | 7/2007 | Richlen et al. | |
| 7,591,810 B2 | 9/2009 | Morman et al. | |
| 7,993,320 B2 | 8/2011 | Hornung et al. | |
| 2004/0116886 A1 | 6/2004 | Van Gompel et al. | |
| 2005/0148965 A1* | 7/2005 | Richlen et al. | 604/367 |
| 2009/0143756 A1 | 6/2009 | Hornung et al. | |
| 2009/0157029 A1* | 6/2009 | Hornung et al. | 604/367 |
| 2011/0251576 A1 | 10/2011 | Ando et al. | |
| 2012/0035572 A1 | 2/2012 | Ichikawa et al. | |
| 2012/0046632 A1 | 2/2012 | Malowaniec | |
| 2012/0078213 A1* | 3/2012 | Nakaoka et al. | 604/385.25 |
| 2012/0215191 A1* | 8/2012 | Takino et al. | 604/365 |

FOREIGN PATENT DOCUMENTS

| | | |
|---|---|---|
| DE | 10 2007 056 126 A1 | 5/2009 |
| DE | 102007055628 | 5/2009 |
| DE | 102010048932 | 4/2012 |

(Continued)

*Primary Examiner* — Susan Su
(74) *Attorney, Agent, or Firm* — Henry M. Feiereisen LLC.

(57) ABSTRACT

In an incontinence article in pant form, a crotch section is connected to stomach and back sections in respective overlapping regions of the crotch section and the stomach section and the crotch section and the back section, by means of multiple adhesive strips extending spaced apart from one another in a transverse direction of the incontinence article, whereby visually and/or tactilely perceivable structures are formed on the outer visible side of the incontinence article in the respective overlapping regions, which structures correspond in their course to a course of the adhesive strips.

19 Claims, 9 Drawing Sheets

(56) References Cited

FOREIGN PATENT DOCUMENTS

| EP | 1 787 610 | 5/2007 |
| EP | 1 818 030 | 8/2007 |
| EP | 2 241 296 A1 | 10/2010 |
| EP | 2 377 500 A1 | 10/2011 |
| WO | WO 2011/055546 A1 | 5/2011 |

\* cited by examiner

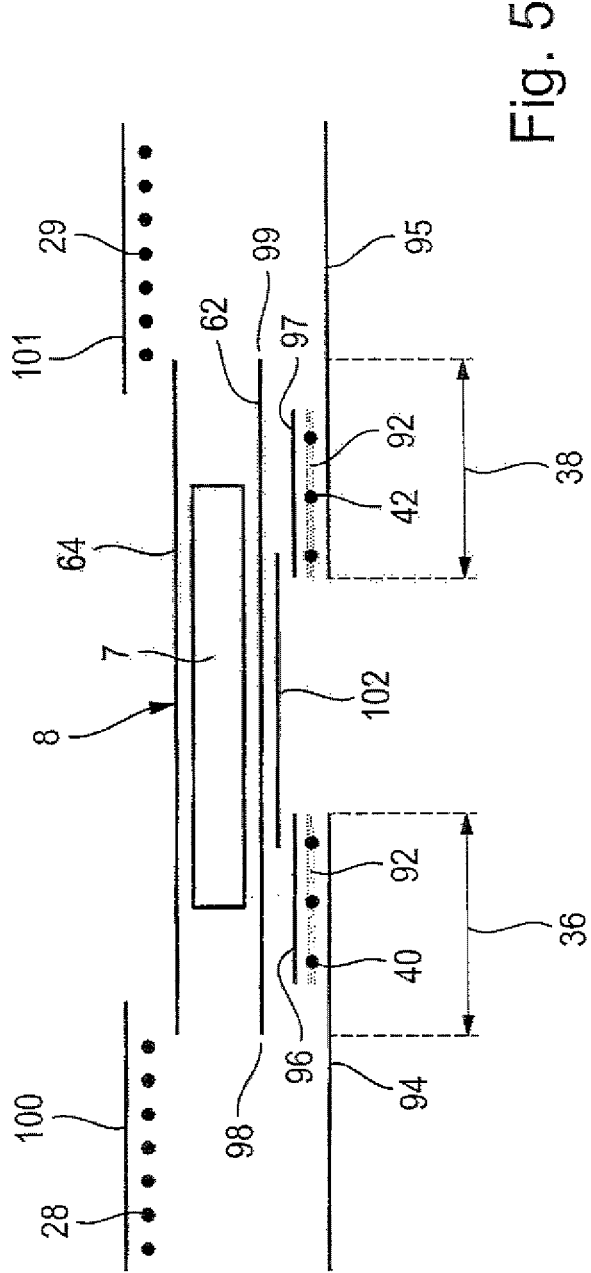

INCONTINENCE ARTICLE IN PANT FORM

CROSS-REFERENCES TO RELATED APPLICATIONS

This application claims the priority of German Patent Application, Serial No. 10 2012 208 392.8, filed May 18, 2012, pursuant to 35 U.S.C. 119(a)-(d), the disclosure of which is incorporated herein by reference.

This application claims the benefit of prior filed U.S. provisional Application No. 61/659,438, filed Jun. 14, 2012, pursuant to 35 U.S.C. 119(e), the disclosure of which is incorporated herein by reference.

BACKGROUND OF THE INVENTION

The invention relates to an incontinence article in pants form for absorbing bodily excretions.

The following discussion of related art is provided to assist the reader in understanding the advantages of the invention, and is not to be construed as an admission that this related art is prior art to this invention.

Incontinence articles in pants form principally differ from openable and closable incontinence articles in conventional diaper form, in that the waist circumference is already predetermined by the pant form, and the adjustment to different body sizes based on a number of basic sizes is achieved in that the article can be elastically stretched. For this, elastifying means, in particular in the form of bands or threads, often also referred to as Lycra—threads, are usually connected in a pre-tensioned state (Stretch-Bond-Method) to chassis materials of the incontinence article i.e., they are fixed in a pre-tensioned state on the chassis materials for example by means of glue. Due to their pre-tension, these elastifying means bundle chassis materials together, thereby forming plications, which typically extend transverse to the direction in which the elastifying means are pre-tensioned, i.e. in this case in longitudinal direction of the article. The incontinence article or the elastified chassis materials of the incontinence article can then be elastically stretched again when the user puts on the incontinence article like a pant. The chassis materials themselves on the other hand are preferably non-elastic and can thus be guided in a well defined manner in the transport plane in a flat or evenly spread out state so that the elastifying means can then be attached with a defined pre-tension.

For non-detachably connecting the stomach section or the back section with the crotch section in the respective overlapping region, a full-surface joining, in particular gluing, or a joining over less than the entire surface can be selected. In known hygiene articles, often times in order to join large surface regions, adhesive is applied over the entire surface, or adhesive is applied in spiral form essentially over the entire surface through nozzles. There are also hygiene articles, however in which a different approach is taken; thus US 2004/0116886 A1 for example teaches not to join large surface areas of the respective overlapping region; This is intended to retain freedom of shape and flexibility of the components in the overlapping region, and not to be influenced negatively by a joint.

U.S. Pat. No. 7,250,549 teaches to provide respective areas with different adhesive properties in the respective front or rear overlapping region. A waist-averted region i.e., a region facing the center of the crotch section and extending in transverse direction is to have a greater mass per area of the adhesive than a region which is located waist-side relative to this region. The regions can be coated with adhesive over their entire surfaces or linearly, spirally or punctiform.

U.S. Pat. No. 7,591,810 B2 teaches to connect the crotch section and the stomach section or the crotch section and the back section only very partially to one another.

As mentioned before, the two-dimensional elastification of the stomach- and back band in transverse or waist-circumferential direction leads to an elastic bundling up of the chassis materials, which enables an adjustment of the incontinence article in pant form to the respective body circumference in the first place. As a result of this bundling up, pleatings form which can also be perceived when they extend more or less than in the longitudinal direction of the hygiene article. The course of the elastifying means which extend in transverse or waist circumferential direction can also be recognized. In the front and rear overlapping region, these pleatings which extend in the longitudinal direction of the incontinence article, are less pronounced due to the stiffening effect of the crotch section; in known articles, they can typically still be perceived at this location. Because elastifying means also extend in the overlapping region in approximately transverse direction, because they typically are supplied in the machine direction of the stomach and back section i.e., in transverse direction, and switch sides relative to the incontinence article, further structures result which can at least be optically perceived. Even though the mentioned elastifying means no longer possess their elastifying effect in the respective overlapping region of crotch section and stomach section or crotch section and back section, i.e., they are deactivated in an appropriate manner, in particular cut, the course of the elastifying means in the finished product can be recognized. A structure forms, which approximately extends in the transverse direction, and can be optically perceived and creates a technical appearance of the article.

It would therefore be desirable and advantageous to provide an incontinence article with an improved connection between the three components, i.e., the connection of crotch section and stomach section in the front overlapping region and of crotch section and back section in the rear overlapping region with regard to the aforementioned aspects, which connection reliably withstands on one hand the stress situations that occur during use of the incontinence article and on the other hand, results in an esthetically pleasing appearance of the incontinence article with regard to the aforementioned aspects.

SUMMARY OF THE INVENTION

According to one aspect of the present invention, an incontinence article in pant form for absorbing bodily excretions, includes a stomach section; a back section, spaced apart from the stomach section in a longitudinal direction of the incontinence article along a longitudinal center axis, wherein the stomach section and back section have respective lateral seam regions and are joined at the respective lateral seam regions thereby forming a stomach- and back band which is continuous in a transverse direction of the incontinence article, and has a circumferentially closed waist opening; a crotch section having an absorption body and extending in the longitudinal direction between the stomach section and the back section, wherein the crotch section overlaps with the stomach section and the back section in respective overlapping regions and is non-detachably connected to the stomach section and to the back section in the respective overlapping regions, wherein the stomach section, back section and crotch section together delimit leg openings of the incontinence article, wherein the stomach and back section have respective crotch-side regions facing the leg openings; first elastifying means extending in spaced apart and parallel relationship to one another in the transverse direction in the stomach section and back section, thereby two-dimensionally elastifying the stomach section and the back section; and second elastifying means extending in the respective crotch-side regions of the stomach and back sections, in particular from the respective lateral seam regions towards the longitudinal center axis into the respective overlapping regions of the crotch section and back section (in the following also referred to as rear overlapping region) and of the crotch section and stomach section (in the following also referred to as front overlapping section), wherein the crotch section is none-detachably connected to the stomach section and to the back section with plural adhesive strips provided in the respective overlapping regions, and extending in parallel relationship to one another in the transverse direction of the incontinence article and are separated from each other by adhesive-free strips, thereby forming visually and tactilely perceivable structures on an outer visible side of the incontinence article in the respective overlapping regions, and wherein a course of the structures corresponds to a course of the adhesive strips and the adhesive-free strips.

Thus, a three-component incontinence article is involved, wherein the stomach section, the back section and the crotch section form these three components. The stomach section and the back section as well as the crotch section are fed into or transported in a manufacturing device as separate components. Typically, the components are guided in a respective transport plane in a flat or evenly spread out state. The stomach section and the back section are transported in the later transverse direction of the incontinence article while being spaced apart from one another in the later longitudinal direction of the incontinence article. Thus, the later transverse or waist-circumferential direction of the incontinence article extends in the machine direction of the manufacturing device. The aforementioned distance between the stomach section and the back section is then bridged by applying the crotch section as third component, wherein an overlapping region between crotch section and stomach section and between crotch section and back section is formed, wherein the three components are permanently joined with each other in the respective overlapping region. Finally, the stomach section and the back section are interconnected at lateral seam regions on both sides as mentioned above. Such an incontinence article is for example known from DE 10 2007 055 628 A1.

According to the invention it was discovered that the application of adhesive according to the invention in the form of multiple adhesive strips that extend in transverse direction, in conjunction with the mostly nonwoven-based or nonwoven-containing materials or composite materials of the stomach section and the back section and as the case may be also the crotch section, enable formation of a visually and/or tactilely perceivable structure on the outer visible side of the overlapping region, which harmonizes with or corresponds to the optically and/or tactilely perceivable course of the elastifying means in the respective overlapping region. In this way, the course of the elastifying means can be concealed in the overlapping region, where these elastifying means are also often deactivated, so that they can no longer be distinguished from the structure resulting from the adhesive. This is esthetically pleasing.

This structure, which extends in the respective overlapping region in transverse direction and can be visually or tactilely perceived, is thus formed by the strip-shaped application of adhesive. This results from the fact that strip-shaped adhesive-free areas of the stomach section and the back section can rise up from the material of the crotch section, while the strip shaped regions to which adhesive was applied are held down. This phenomenon is further supported in that the chassis materials of stomach section and back section are usually fibrous, nonwoven materials, which in a manner of speaking are able to three-dimensionally absorb the adhesive. This leads to a further stiffening which on one hand counteracts the formation of pleatings that extend in longitudinal direction, and on the other hand facilitates the formation of a structure that extends in transverse direction. As a result, the formation of this structure according to the invention conceals or makes unrecognizable, the elastifying means which approximately extend in transverse direction in the overlapping region and which may be deactivated. These elastifying means are less readily perceived as technical elements than in known incontinence articles. The general longitudinal pleating in the front and rear overlapping region of the chassis materials is also reduced due to the contracting effect of elastifying means that extend in waist-circumferential direction.

According to the invention, it was also found, that in the case of such a non-detachable joining of the components, the amount of the adhesive materials required therefore can be reduced compared to an application of adhesive over the entire surface or for example compared to a spiral-shaped application of the adhesive, without resulting in disadvantages. It was further found, that when using multiple adhesive strips which extend in transverse direction, the forces which typically occur during use of the hygiene article in longitudinal direction and which are introduced into the overlapping region or via the overlapping region from the crotch section into the stomach section or into the back section can be absorbed likewise well when the multiple adhesive strips essentially extend over the entire extent of the respective overlapping region. This does not mean however, that the adhesive strictly has to extend up to the respective geometric border of the overlapping region; rather, it is preferred, that the adhesive retains a defined distance to the geometric border of the overlapping region in the range of one or a few millimeters, in order to avoid that the adhesive leaks from the overlapping region and contaminates the manufacturing device or becomes visible on the finished product. It is further advantageous, that the multiple adhesive strips extend in the transverse direction i.e., especially with regard to the fact that forces of the soaked absorption body due to gravity typically act in the longitudinal direction i.e., transverse to the extent of the adhesive strips. These forces, due to the transverse extent of the adhesive strips, can even be transmitted better and more evenly across the respective overlapping region into the waist-circumferential direction of the stomach section and to the back section or respectively, be absorbed by the stomach section and the back section.

The multiple adhesive strips, which extend essentially over the entire respective overlapping region, are typically applied by a so-called contact application, preferably by using template techniques. For this, adhesive application devices known per se can be used, for example the TrueCoat™ system of the company Nordson Deutschland from Erkrath, Germany. The TrueCoat™ system is a slot nozzle surface application device, wherein the slot nozzle application heads are configurable and thus enable a continuous or intermittent application of adhesive. The application of the adhesive by using a sheet metal with strip-shaped recesses is also possible. Advantageously, the adhesive is applied in machine direction of the material tracks that form the stomach section and the back section, i.e., with adhesive strips extending in machine direction, so that the multiple adhesive strips—as mentioned multiple times—extend in the finished product essentially transverse to the longitudinal direction, i.e., in transverse- or waist-circumferential direction.

According to another advantageous feature of the present invention, the adhesive can be applied in the machine direction in a pulsed manner, i.e., glue is actually only applied in the already mentioned overlapping regions between crotch section and stomach section or between crotch section and back section.

According to another advantageous feature of the present invention, the width of adhesive strips transverse to their extent can be at least 1 mm to at most 5 mm, in particular at most 4 mm and further in particular at most 3 mm and preferably 2 mm.

The width of the adhesive-free strips transverse to their extent is advantageously at least 1 mm to at most 15 mm, in particular to at most 10 mm, in particular two at most 5 mm and further in particular to at most 3 mm.

As mentioned before, it is conceivable that in the respective overlapping region, i.e., the rear and/or the front overlapping region, a wider adhesive strip can be provided border-side. This means, that in a border region of the overlapping region, which in longitudinal direction is waist-side, and/or in a border region of the overlapping region which in longitudinal direction faces away from the waist, a wider adhesive strip, which extends in transverse direction can be provided. This waist-side border region or waist-averted border region of the overlapping region covers respectively at the most 20%, in particular at most 18%, in particular at most 15%, in particular at most 12%, in particular at most 10%, of the longitudinal extent of the respective front or rear overlapping region. The multiple narrow adhesive strips, which extend in transverse direction, are then provided between these border regions. The width of the mentioned border-side adhesive strips transverse to their extent is at least 5 mm, in particular at least 8 mm, in particular at least 12 mm, particular at most 20 mm, in particular at most 16 mm, in particular at most 14 mm. In case, a wider adhesive strip is provided in the overlapping region on only one border, it is advantageous when this wider adhesive strip is provided at the waist-distal border region of the overlapping region, in order to achieve a stable joining at this location, which prevents tearing-in.

According to another advantageous feature of the present invention, the ratio between the width of adhesive strips and the width of immediately neighboring adhesive-free strips can be 0.2-3.0, in particular 0.2-2.0, in particular 0.2 to 1.5, in particular 0.2-1.0, in particular 0.4-0.8, in particular 0.5-0.7. Thus, a finely and evenly distributed succession of adhesive strips and adhesive-free strips is advantageously provided, which enables and even distribution in the joining region and associated therewith a joining stability in the overlapping region and at the same time an even distribution of a possible stiffening due to the adhesive strips.

Also with regard to a possible even and/or tactilely recognizable configuration or structuring as a result of the multiple adhesive strips, it is advantageous when at least those adhesive strips which are located inwardly relative to optional border-side adhesive strips, i.e., in longitudinal direction between border-side adhesive strips, have the same width.

It is further advantageous when the width of the respective adhesive-free strips is the same.

Regardless of the specific configuration or arrangement of the multiple adhesive strips, it is advantageous when the entire surface of the adhesive strips relative to the surface of the overlapping region of the crotch section and the stomach section or of crotch section and back section is 35-60%, in particular 40-55% and further in particular 40-50%.

According to another advantageous feature of the present invention, the mass per area of the adhesive coating in the adhesive strips can be 2-20 g/m², in particular 2-15 g/m², in particular 2-10 g/m², in particular 5-10 g/m², wherein the mass per area in all adhesive strips is preferably the same.

In order to achieve an even transmission of forces resulting from the liquid which was absorbed during use of the hygiene article by the absorption body, into the stomach- and back band which is formed by the stomach section and the back section and is continuous in transverse- or waist-circumferential direction, it is advantageous when the surface of the overlapping region of the crotch section and back section is at least 12%, in particular 15-40%, in particular 15-35%, in particular 15-30%, in particular 20-30%, in particular 22-30% of the surface of the stomach section. It is further advantageous that the surface of the overlapping region of the crotch section and back section is at least 20%, in particular 20-45%, in particular 20-40%, in particular 22-40%, in particular 25-40%, in particular 28-40% of the surface of the back section.

According to another advantageous feature of the present invention, border-side adhesive strips, i.e., a waist-distal and a waist-proximal border-side adhesive strip and in longitudinal direction between these, multiple inwardly located adhesive strips can be provided in the overlapping region of crotch section and stomach section and/or in the overlapping region of crotch section and back section 2 outer, wherein the width of the border-side adhesive strips is greater than the width of the inwardly located adhesive strips, and is in particular at least four times, in particular at least five times, and further in particular at most eight times, in particular at most seven times the width of the inwardly located adhesive strips. It is also conceivable, that on a respective waist-side or waist-averted border region of the respective overlapping region, multiple wider border-side adhesive strips are provided, so long as the border region does not exceed the previously explained dimensions in the longitudinal direction.

According to another advantageous feature of the present invention, at least 8, in particular at least 10 adhesive strips can be provided in the overlapping region of stomach section and crotch section, and in the overlapping region of the back section and crotch section, at least 15, in particular at least 18 and further in particular at least 20 adhesive strips are provided.

According to another advantageous feature of the present invention, the previously mentioned second elastifying means, which are provided in a crotch-side region of the stomach section and the back section, which crotch-side region faces the leg openings, fan out arch-like with increasing distance to one another in the direction towards the longitudinal center axis and in the direction toward the respective overlapping region. In this way, the return force acting in the surface of the crotch-side region of the stomach section and the back section, which crotch-side region faces the leg openings, can be influenced. In this way, the return force can be reduced in the direction towards the longitudinal middle axis.

This fanning-out of the second elastifying means can also be quantitatively described in more detail. For example, the second elastifying means of the back section shown in FIG. 1 have a minimal distance of 3 to 8 mm to each other (distance between immediately neighboring elastifying means) and at a border of an absorption body or a longitudinal border of the crotch section have a maximal distance to one another (distance between immediately neighboring elastifying means) of 7 to 35 mm. A degree F. of the fanning-out can be defined as follows:

$$F=(A-B)/B*100\%.$$

This fanning-out degree advantageously is between 50 and 900%, in particular between 100 and 700%, and further in particular between 150 to 550%. Advantageously, it is greater in the back section than in the stomach section. The variables A and B are defined as the distance of the in longitudinal direction outermost second elastifying means to the in longitudinal direction innermost second elastifying means (i.e., not the distance between immediately neighboring elastifying means), i.e. A as the maximal distance, in particular at the longitudinal border of the crotch section, and B as the minimal distance, in particular in the lateral seam region.

According to another advantageous feature of the present invention, the first and/or the second elastifying means in the overlapping region of crotch section and stomach section and in the overlapping region of crotch section and back section, can extend parallel to the adhesive strips. Typically, the elastifying means are introduced so that they extend endlessly in transverse- or waist-circumferential direction i.e., in the machine direction of the flat material tracks of the future stomach section and back section. Thus, they extend at least initially continuously over the entire transverse extent of the incontinence article. In this way, the elastifying means typically traverse the absorption body underneath in the respective front or rear overlapping region of the crotch section and the stomach section or of crotch section and back section so that the absorption body of the crotch section comes to lie above the elastifying means. In this case, it is particularly expedient, when the elastifying means no longer posses their elastifying effect, at least where they traverse the absorption body underneath; for this purpose, they can be cut, in particular multiple times, in this region along their transverse extent or can be de-elastified by other means for example by ultrasound. Nevertheless, the course of the originally introduced elastifying means as well as the elastifying means which have been deactivated or de-elastified in the respective overlapping region, can be recognized from outside the incontinence article. A particular advantage of the invention is that this can be concealed by providing multiple narrow adhesive strips as mentioned before.

The previously mentioned arch-shaped fanning-out can preferably be configured so that a distance of the second elastifying means to each other in a respective lateral seam region is 3 two 8 mm, and further inwardly in the direction towards the longitudinal center axis in the region of a border of the absorption body is between about 7 and 35 mm, in particular between 12 and 30 mm.

Preferably, thread-shaped or band-shaped elastifying means such as rubber threads, polyetherpolyurethane threads or polyesterolyurethane threads, preferably elastic threads such as Lycra®—or Spandex® threads are used as first and/or second elastifying means. The first elastifying means preferably have a thread length of 40-1500 dtex, in particular 500-1400 dtex, in particular 800-1400 dtex, in particular 1000-1400 dtex, further in particular 1100-1400 dtex. The second elastifying means preferably have a thread Strength of 500-1000 dtex, in particular of 600-1000 dtex, further in particular 700-900 dtex.

The thread strength of the elastifying means is expressed in the unit dtex (1 dtex=1 g/10,000 m). The thread strength is determined according to the testing guidelines BISFA, the International Bureau for the Standardization of man-made Fibres, Test methods for bare elastane yarns, edition 1998, chapter 5: "Determination of linear density". The thread strength or linear density is determined by determining the mass of a test specimen having a known thread length of 1,000 mm (cut under a standard pre-tension of 0.1+/−0.01 mN/dtex) after a conditioning under standard conditions (23° C.+/−2° C., 50%+/−5% relative humidity) in the relaxed state.

The thread strength (in dtex) is calculated from the quotient of the mass (in g) divided by the length of the section (in m) multiplied by the factor 10,000.

For this, five sections of the thread-shaped or band-shaped elastifying means having a length of 1,300 mm are cut off from the role or package under a tension that is as small as possible, namely in uneven distances of at least 2 m. These five sections are relaxed so as to be tension-less and are let rest under standard conditions for at least four hours. Then, a test specimen of 1,000 mm+/−1 mm is cut off from the respective 1,300 mm long section, while the section is maintained under a pretension of 0.1 mN/dtex. The cut off test specimens of 1,000 mm length are weighed to an accuracy of +/−1% of their expected mass. For each testing specimen, its thread strength is obtained by multiplying the respective mass with the factor 10,000 in dtex. From the five testing specimen, the arithmetic mean value is calculated which is used as thread strength for the purposes discussed here.

According to another advantageous feature of the present invention, the first and/or second elastifying means can be fixed on the chassis-forming sheath materials of the stomach section and the back section (stretch-bonding-method) under a pre-tension of 2.5-6.0. The pre-tension is defined as the degree of stretching of a stretched elastifying means relative to the unstretched/relaxed original state of the elastifying means in the state of the application and fixing of the elastifying means in the manufacturing machine. The degree of stretching is thus calculated as the ratio of the stretched length L' (=initial length L+ΔL) to the initial length L, i.e., L'/L. The first elastifying means are preferably fixed under a pre-tension of 4.0-6.0, in particular of 4.5-5.5, wherein their pre-tension is preferably greater then the pre-tension of the second elastifying means. The second elastifying means are preferably fixed under a pre-tension of preferably 2.5-5.0, in particular of 3.0-4.5.

The crotch section advantageously includes a liquid-impermeable backsheet-material and a nonwoven topsheet-material, between which the absorption body is arranged. The backsheet-material and the nonwoven-topsheet-material in a manner of speaking form the chassis of the crotch section. In a refinement of the invention, it is advantageous when the backsheet material and/or topsheet material form an overhang over the absorption body and this overhang—in total on both sides of the absorption body, i.e., in total left and right—is at least 25%, in particular 30-50%, further in particular 35-50%, further in particular 38-48%, further in particular 40-45%, of the greatest width of the crotch-section (i.e., relative to the maximal extent of the crotch section in transverse direction).

This relatively great overhang of backsheet material and/or topsheet material on both sides of the absorption body thus means a wide crotch section with a relatively narrow absorption body. This allows providing leg-elastifying means in the crotch section, which extend along the leg openings, and have a relatively great distance to the material rich and with this bending stiff, absorption body. This in turn results in a good sealing and adjustability of the borders of the leg openings on both sides of the crotch section. In this case, the material rich absorption body, which is torsion stiff relative to the thin chassis materials, only interferes with the formation of a liquid-tight leg sealing to a minor degree; forming a liquid-tight leg sealing does therefore not require extremely high tensions which in turn has a positive influence on the wearing comfort of the incontinence article.

According to another advantageous feature of the present invention, the leg-elastifying means end in longitudinal direction at least 10 mm, in particular at least 20 mm, before the second elastifying means. It is particularly advantageous when the leg-elastifying means end in longitudinal direction before the stomach section and/or before the back section. The tension and return force exerted by the leg-elastifying means does therefore not influence the tension conditions provided according to the invention within the crotch-side region of the stomach section and the back section that faces the leg openings, in which the fanning-out, second elastifying means are provided.

Preferably, thread- or band-shaped elastifying means, such as rubber- or polyurethane or polyesterpolyurethane threads are used as leg-elastifying means, preferably elastic threads such as Lycra® threads or Spandex® threads. The leg-elastifying means preferably have a tensile strength of 300-1500 dtex, in particular of 500-1200 dtex, further in particular of 500-900 dtex.

The leg-elastifying means are preferably fixed on the chassis-forming sheath materials of the crotch section under a pre-tension of 1.5-6.0, in particular 2.5-4.5.

According to another advantageous feature of the present invention, the chassis-forming materials of the stomach section and/or back section can include nonwoven materials such as spunbonds, card webs or through-air-bonded card webs. Particularly preferably, the chassis-forming material of stomach section and/or back section includes a spunbond material. The nonwoven materials that are used for the stomach section and/or back section Preferably have a mass per area of 10-30 g/m², further preferably of 15-25 g/m². Particularly preferably, the stomach section and the back section include a spunbond, in particular made of polypropylene, in particular with a mass per area of 15-25 g/m².

Due to their flexibility, low masses per area of the chassis forming materials of stomach section and/or back section, in particular including or being made of nonwoven materials, enable particularly advantageously the formation of the visually and/or tactilely perceivable structures according to the invention.

According to another advantageous feature of the present invention, the crotch section advantageously can include a liquid-impermeable backsheet-material and a nonwoven topsheet material. The backsheet material in particular includes a foil, in particular with a mass per area of 8-20 g/m², in particular 8-16 g/m², further in particular 8-14 g/m². In particular, the backsheet includes a foil which in particular is micro-porous and during use liquid tight but at the same time breathable, i.e. water vapor permeable.

According to another advantageous feature of the present invention, the absorption body can include materials that absorb bodily fluids such as natural or synthetic fibers, in particular cellulose fibers, preferably in the form of cellulose. Preferably, the absorption body also includes superabsorbent materials (SAP), in particular based on surface-cross-linked, partially neutralized polyacrylates.

The crotch section or the longitudinal borders of the crotch section, which delimit the leg openings, can be configured to have a straight or arched contour. The crotch-facing transverse borders of stomach section and back section, which also delimit the leg openings, are advantageously configured to have an arched contour.

BRIEF DESCRIPTION OF THE DRAWING

Other features and advantages of the present invention will be more readily apparent upon reading the following description of currently preferred exemplified embodiments of the invention with reference to the accompanying drawing, in which:

FIG. 5 shows a schematic sectional view of the relevant individual components of the chassis materials along the longitudinal center axis of the incontinence article;

DETAILED DESCRIPTION OF PREFERRED EMBODIMENTS

Figure 1:
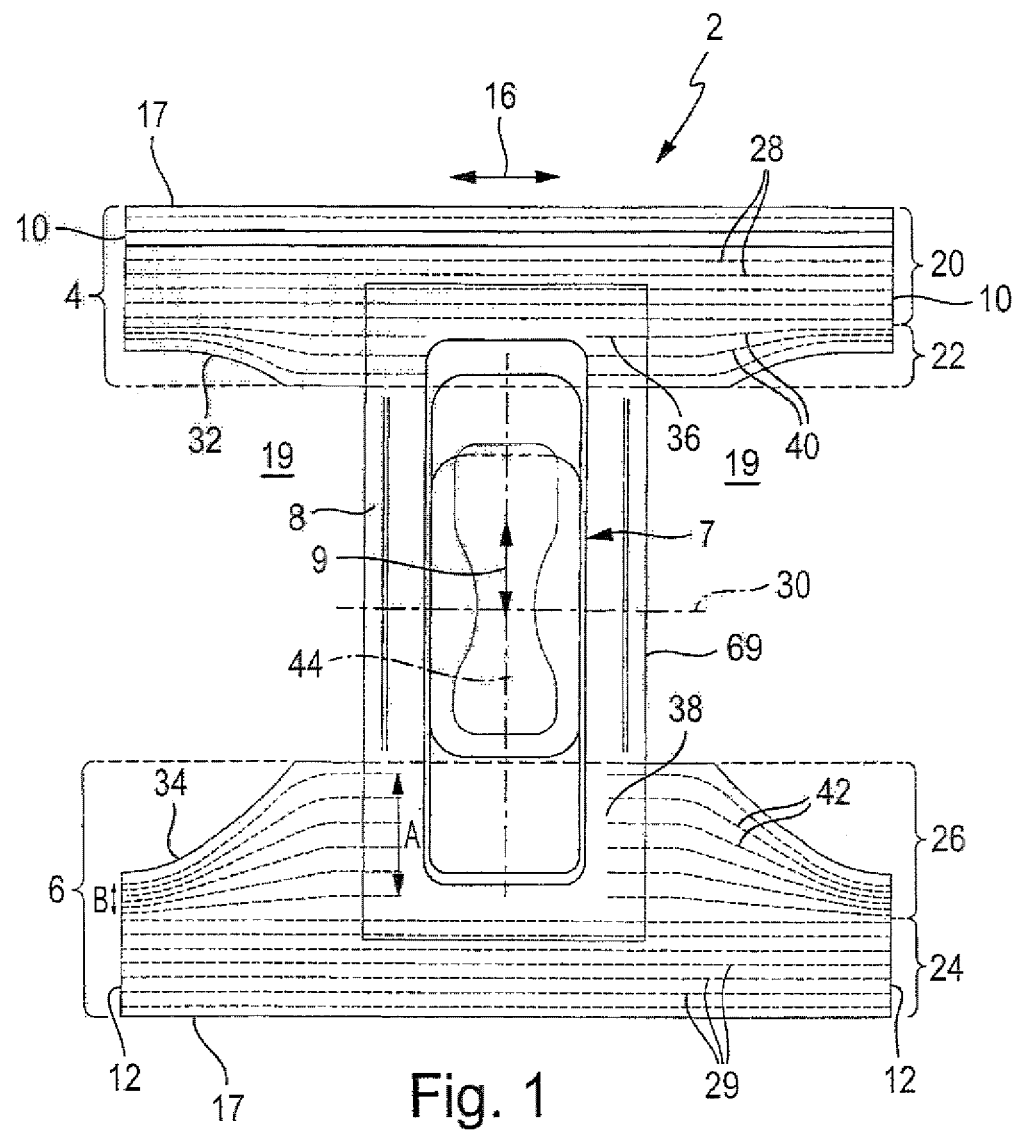
FIG. 1 shows a top view onto an incontinence article according to the invention, wherein a stomach section, a back section and a crotch section of the incontinence article are not yet joined for forming a pant form but are shown in a spread out and evenly stretched out state.

Throughout all the Figures, same or corresponding elements are generally indicated by same reference numerals. These depicted embodiments are to be understood as illustrative of the invention and not as limiting in any way. It should also be understood that the drawings are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

The Figures show an incontinence article in pant form, overall designated with the reference numeral 2, for absorbing solid and liquid bodily excretions. The incontinence article 2 is composed of three components which can essentially be manufactured independently i.e., a front stomach section 4, a rear back section 6, and a crotch section 8 which has an absorption body 7 and is located between the stomach section 4 and the back section 6, wherein the crotch section 8 extends in a longitudinal direction 9 of the incontinence article 2 and overlaps with a substantial surface portion of the stomach section 4 on one hand, and of the back section 6 on the other hand, and is non-detachably connected by the manufacturer in the overlapping region in a manner to be described in more detail below. As can be seen from FIG. 1, this leads to an H-shaped basic structure of the incontinence article. For forming the pant form, the interconnected components shown in FIG. 1 are then connected to one another at respective lateral longitudinal border sections 10, 12 of the stomach section 4 and the back section 6, also by the manufacturer, by conventional joining methods, thereby forming lateral seam regions 14 on both sides. In this pant form of the incontinence article, which is manufactured by the manufacturer, the stomach section 4 and the back section 6 extend in a transverse- or waist-circumferential direction 16 continuously and thus define with their waist border 17 a waist opening 18 which is closed in waist-circumferential direction; further, together with the crotch section 8 they delimit leg openings 19, through which the user can put on the incontinence article like a pant.

The stomach section 4 can be divided into a waist-side region 20 and into a crotch-side region 22, which faces the leg openings 19. The back section 6 can be divided correspondingly i.e., also in a waist-side region 24 and a crotch-side region, which faces the leg openings 19.

In the waist-side region 20 of the stomach section 4 and in the waist-side region 24 of the back section 6, first elastifying means 28, 29 are provided, which may be Lycra-threads, and which are connected with the flat materials (chassis materials) of the stomach section 4 and the back section 6 in the so-called stretch-bond-method. These first elastifying means 28, 29 extend in transverse- or waist-circumferential direction 16 from one lateral seam region 14 to the other.

The respective crotch-side sections 22 and 26 of the stomach section 4 or of the back section 6 which face the leg openings 19 each have a border contour 32 or 34 which deviates from the transverse- or waist-circumferential direction 16 and which extends towards a transverse center axis 30 of the crotch section 8. This border contour 32, 34 is also arch-shaped in the representation according to FIG. 1 and therefore suited for delimiting the leg openings 19.

Through this extent of the crotch-side region 22 or 26 which faces the leg openings, a relatively great overlapping region 36, 38 between the crotch section 8 and the stomach section 4 or back section 6 is realized, which is important with regard to a tear-resistant connection of crotch section 8 and stomach section 4.

The respective crotch-side region 22, 26 of the stomach section 4 or the back section 6 which crotch-side region 22, 26 faces the leg openings 19, is also configured elastified and is provided with second elastifying means 40 or 42. The second elastifying means 40, 42 extend, in each case starting from the lateral seam regions 14, in the direction towards a longitudinal center axis 44 of the incontinence article. As can be seen from FIG. 1, the second elastifying means 40, 42 fan out in the direction towards the longitudinal center axis 44, i.e., with increasing distance to one another in the direction towards the longitudinal center axis 44. The second elastifying means 40, 42 pass underneath the crotch section 8. In the region below the absorption body 7, they may be deactivated i.e. they may not posses their elastifying effect.

Figure 2A:
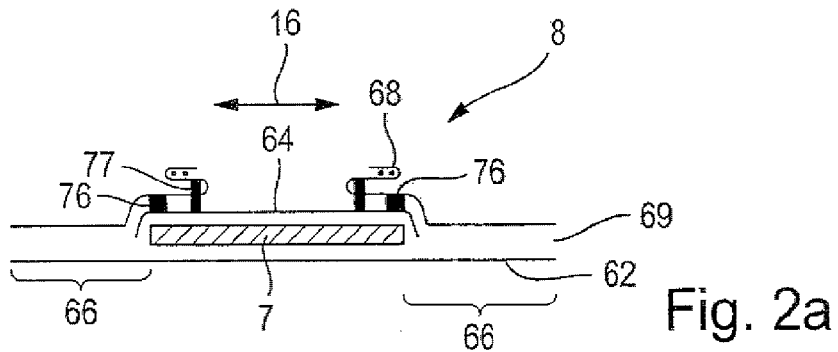
FIGS. 2a, b show schematic sectional views of the crotch section in the region of the transverse centerline or in the overlapping region of crotch section and back section.
Figure 2B:
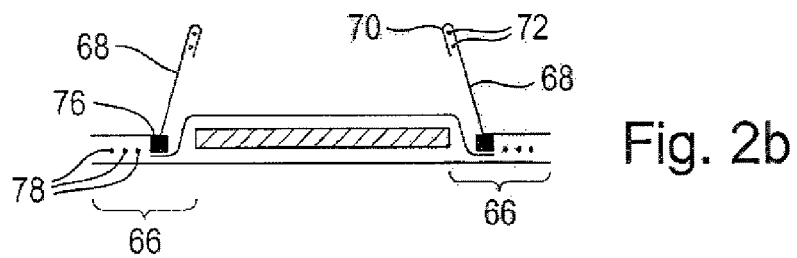

As can be seen from FIGS. 2 a, b, the crotch section 8 includes a liquid-impermeable backsheet material 62, which can in particular be formed by a breathable, but liquid-tight foil material and a preferably nonwoven-based topsheet material 64. The absorption body 7 (only shown schematically) is arranged between the backsheet material and the topsheet material. In the exemplary shown case, the backsheet material 62 forms an overhang 66 over the absorption body 7 in transverse direction 16. The topsheet 64 protrudes over the absorption body 7 in transverse direction 16 only to a relatively small degree and an upright barrier means 68 is provided on both sides of the absorption body 7. The barrier means 68 extends in a longitudinal direction 9, and is typically referred to as upright cuff element and is preferably made of a hydrophobic, in particular liquid-impermeable nonwoven material which extends in transverse direction 16 as far as to lateral longitudinal borders 69 of the crotch section 8. The distal ends 70 of the barrier means 68 are provided with further elastifying means 72 which raise the barrier means 68 during use of the incontinence article relative to the skin surface of the user. The lateral barrier means 68 are fastened on the topsheet 64 or onto themselves in a C-shape-folded configuration via schematically indicated fixations 76, 77. Outside of the absorption body 7 i.e., in the region of the protrusion 66, leg-elastifying means 78 are provided, which preferably extend at a defined distance to the material-rich and with this rather bending stiff absorption body 7, in order on one hand, to prevent exerting additional stretching or distortion forces on the absorption body, which might negatively influence the absorption properties of the absorption body and on the other hand to realize a liquid-tight leg sealing, which to the most degree is not influenced by the absorption body. These leg-elastifying means 78 end in longitudinal direction 9 at a significant distance of in particular 10 mm, preferably at least 20 mm before the second elastifying means 40 and 42 of the stomach section 4 or the back section 6. Preferably, these leg-elastifying means 78 end in longitudinal direction 8 before the stomach section 4 and the back section 6.

Figure 4:
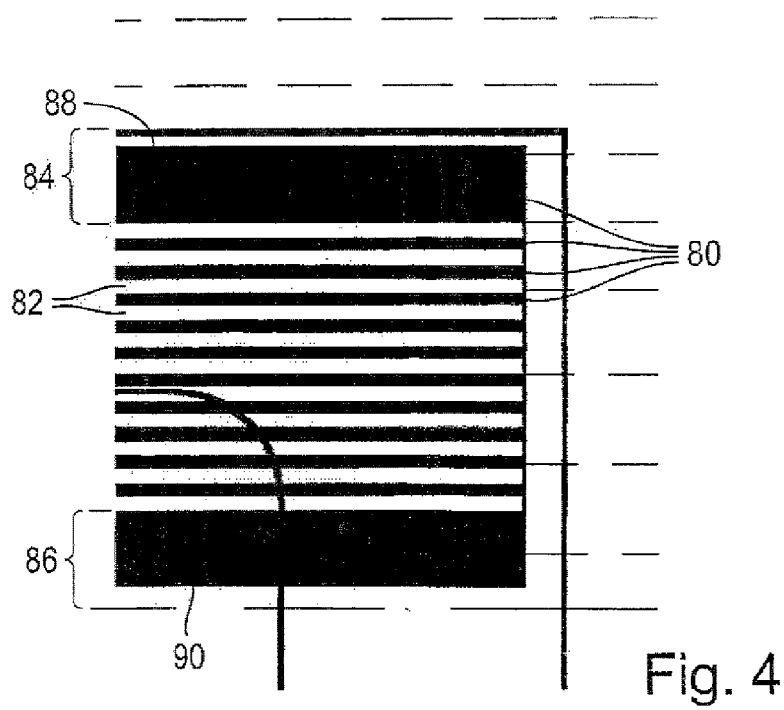
FIG. 4 shows an enlarged representation of a section in the region of the overlapping region of crotch section and stomach section or crotch-section and back section of the incontinence article according to FIG. 3.
Figure 3:
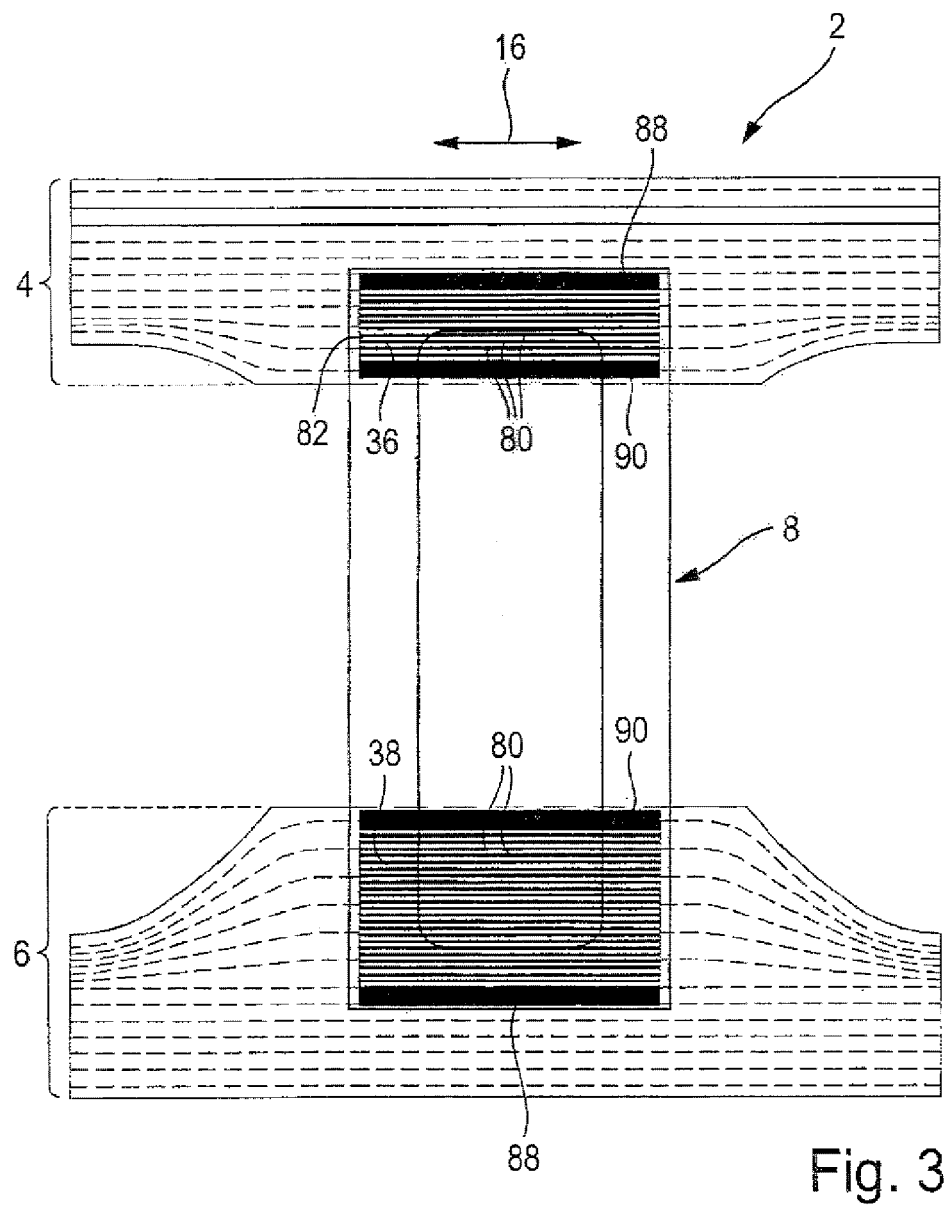
FIG. 3 shows a representation corresponding to FIG. 1, illustrating the fixing of the crotch section with the stomach section and the back section by means of adhesive strips.

In the following, the fixing of the crotch section 8 in the front overlapping region 36 with the stomach section 4 and in the rear overlapping region 38 with the back section 6 is described. As can be seen in FIGS. 3 and 4, for this purpose, adhesive is not applied to the entire surface, but multiple adhesive strips 80 are provided in the overlapping region and extend in transverse direction 16 and parallel to one another and are spaced apart by adhesive-free strips 82. The adhesive strips 80 occupy or overlap essentially the entire respective overlapping region 36, 38. In the exemplary shown, however, not strictly required case, broader adhesive strips 88 and 90 are provided in a border region 84 and a border region 86 of the respective overlapping region 36, 38, which border region 84 is located waist-side in longitudinal direction and which border region 86 faces away from the waist in longitudinal direction. The respective border-side i.e., waist-facing and waist-distal adhesive strips 88, 90 have a greater width than the multitude of adhesive strips 80 which are located inwardly and between the adhesive strips 88, 90. In an exemplary embodiment, the width of the border-side adhesive strips 88, 90 transverse to their extent is 14 mm, the width of the inwardly located adhesive strips 80 is 2 mm and the width of the adhesive-free strips 82 is 3 mm. In the exemplary and preferred shown case, the inwardly located adhesive strips 80 preferably all have the same width and the distances between them i.e., the width of the adhesive free strips 82 are preferably also the same. Nevertheless, the same explanations set forth in the beginning apply with regard to the dimensions and the conditions described there, as well as with regard to the mass per area of the adhesive coating of the adhesive strips. The surface of the front and rear overlapping region 36, 38 relative to the surface of the stomach section 4 or the back section 6 also lies within the previously explained preferred ranges.

It can further be seen from FIG. 3 in conjunction with FIG. 1 that the second elastifying means 40, 42 in the respective overlapping region 36, 38 extend parallel to the adhesive strips 80. In the exemplary shown case, some of the first elastifying means 28 also extend in the front and rear overlapping region 36, 38 (however on the body-facing side of the crotch section). The second elastifying means 40, 42 were also introduced so as to be continuous in the transverse direction 16; they are de-elastified in the respective overlapping region 36, 38 by the aforementioned measures. Even though the second elastifying means remain visible also in the de-elastified state—as explained above, they are concealed by the multitude of adhesive strips 80, thereby reducing their visibility.

In the preferred shown case, the second elastifying means are fixed in a glue bed 92 between chassis material layers 92 and 96 or 95 and 97 (c.f. FIG. 5). The glue bed 92 is applied on one of the chassis material layers 94, 96 or 95, 97. Then, the second elastifying means 40, 42 are placed on or introduced preferably in an endless manner and covered and laminated by the further chassis material layer. In this way, the second elastifying means 40, 42 are fixed and the chassis material layers 94 and 96 or 95 and 97 are joined to each other over their entire surfaces. The body-averted chassis material layer 94, 95 is a breathable fiber nonwoven material, which corresponds to the extent of the stomach section 4 or back section 6. The chassis material layer 96, 97 is an inwardly located fiber nonwoven material which is recessed relative to the chassis material layer 94, 95. In the preferred shown case, it ends in longitudinal direction 9 before the longitudinal end 98, 99 of the crotch section 8.

In the exemplary and preferred shown case, the first elastifying means 28, 29 are fixed between the body averted chassis material layer 94 or 95 and a further body-facing chassis material layer 100, 101 by single-strand application of adhesive. The further chassis material layer 100, 101 is again formed by a nonwoven material. The body-averted and the body-facing chassis material layers are exclusively interconnected by the first elastifying means 28, 29 to which adhesive has been individually applied i.e., only along the extent of these first elastifying means 28, 29. The skin friendly nonwoven materials are therefore not fixed to one another over their entire surfaces, but can detached from one another and, in particular as a result of the elastifying effect, can form pleatings and cuffs. In the preferred shown case, the body-facing chassis material layer 100, 101 extends in the stomach section 4 as well as in the back section 6 over the respective longitudinal end 98, 99 of the crotch section 8 on its body facing-side. It thus overlaps this material transition and in this way prevents an unevenness that leads to skin irritation.

Further, it can be seen in FIG. 5 that the backsheet 62 of the crotch section 8 has a coating 102 on its body-averted side. This coating 102 is a fiber nonwoven coating of the substantially liquid-impermeable backsheet 62. The coating 102 extends in longitudinal direction 9, however, not over the entire longitudinal extent of the backsheet 62 but instead ends relatively short within the front and rear overlapping region 36, 38. Outside of the overlapping region, the coating 102 is provided over the entire extent of the body-averted side of the back sheet 62. The coating 102 is preferably composed of a nonwoven material, in particular of a spunbond material, in particular of polypropylene, in particular with a mass per area of 10-20 g/m$^2$, in particular of 12-17 g/m$^2$.

Figure 6:
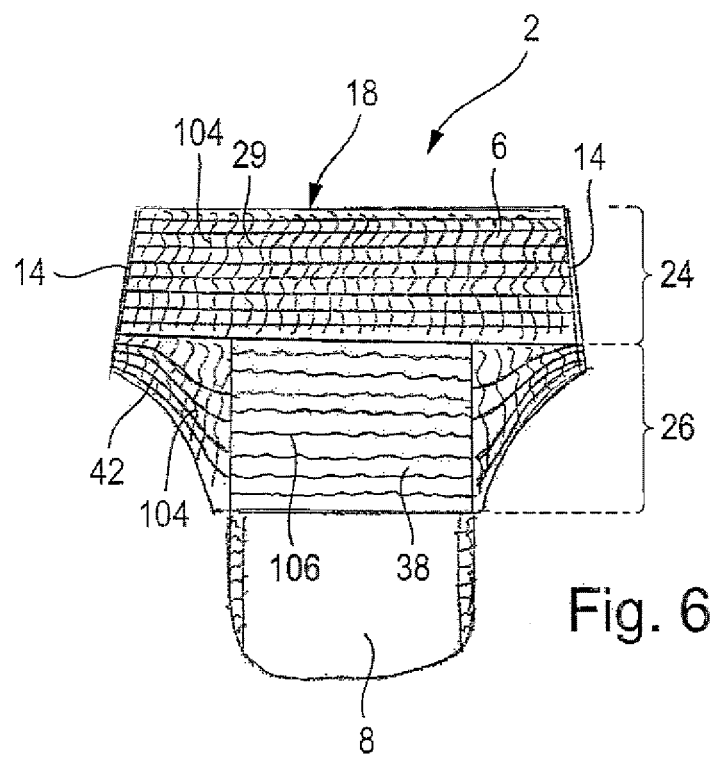
FIG. 6 shows a schematic view of the incontinence article in its final configuration.

FIG. 6 shows a schematic view of an incontinence article according to the invention in the finished configured state in which the stomach section 4 and the back section 6 are joined to one another, forming lateral seam regions 14. Only schematically shown are pleatings or cuffs 104 formed as a result of the contracting effect of the first and second elastifying means 28, 29, 40, 42, resulting from the fixing of the elastifying means in the pre-tensioned state on the chassis materials (stretch bond method). As a result of the multitude of relatively fine adhesive strips 80 in the respective overlapping region 36, 38 of crotch section 8 and stomach section 4 or back section 6, a visually and/or tactilely perceivable structure 106 is formed in the outer visible side of the incontinence article in the respective overlapping region 36, 38 which is here only shown as outline. According to the invention, it was found that the adhesive applied in strip-shape enters into the three-dimensional porous and also breathable configured fiber nonwoven materials, which are typically used as chassis materials, and leads to such an optical and/or tactilely perceivable structure 106, which can be advantageous as mentioned before. In addition, the connection of the crotch section 8 and stomach section 4 or back section 6 by the multitude of relatively narrow adhesive strips 80 leads to a very cost-effective use of adhesive while at the same time nevertheless providing the required holding forces for securely joining the three components to one another.

Figure 7:
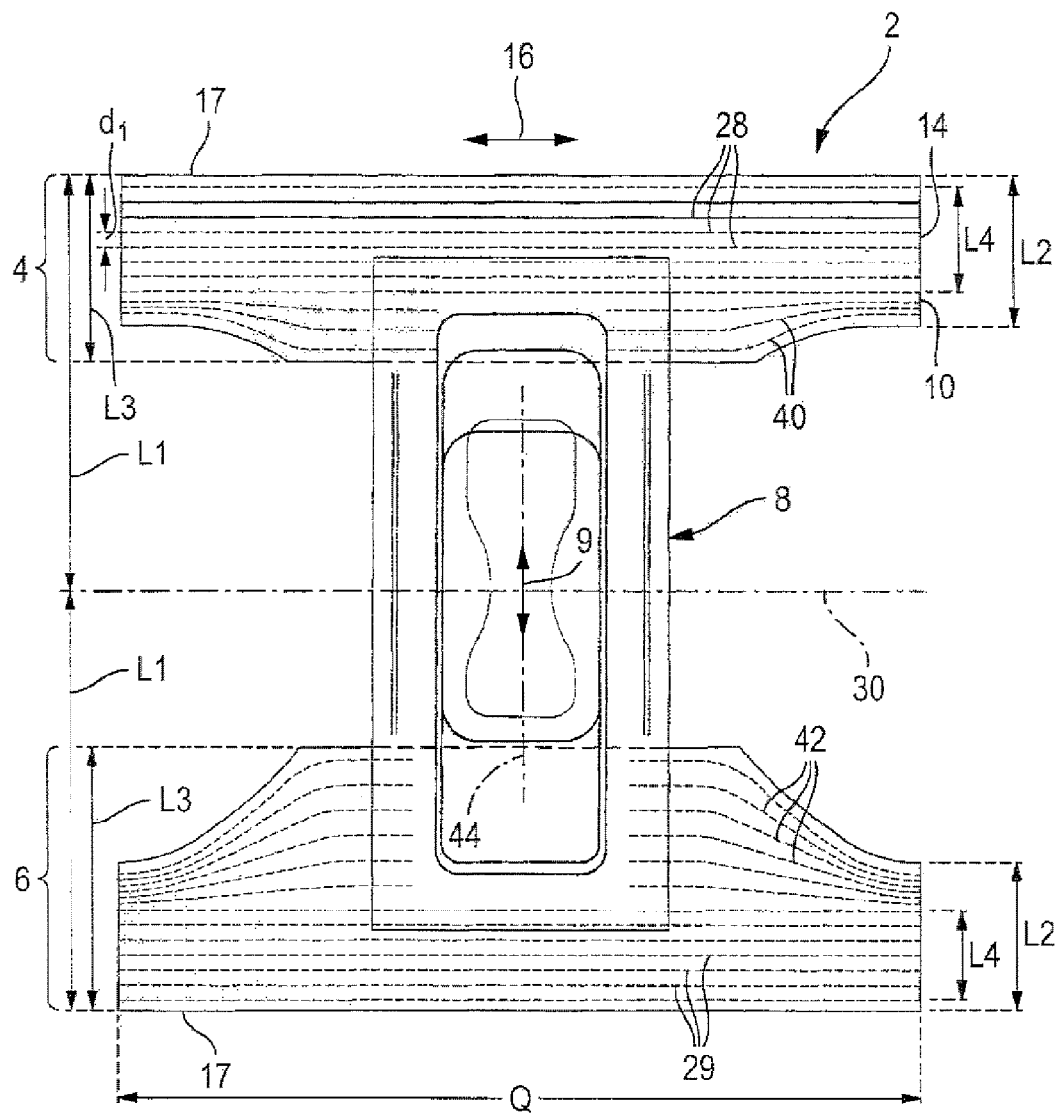
FIG. 7 shows a representation corresponding to FIG. 1, illustrating dimensions.

FIG. 7 explains the measurements, dimensions and ratios of the incontinence article according to the invention. It can be seen that the position of the transverse center axis 30 divides the overall length of the incontinence article in half in the flatly spread out state (according to FIG. 1). The transverse center axis 30 also forms a first folding axis 16 which extends in transverse direction 16, and about which the components are folded inside the manufacturing machine in order to arrange the longitudinal border sections 10, 12 of the stomach section 4 and back section 6 on top of one another for fixing and forming lateral seam regions 14 on both sides. Typically, this occurs by guiding endless, flat materials, which form the respective stomach section 4 and back section 6 i.e., even before the separation of the articles. The length L1 between the transverse center axis 30 and the respective border of the waist 17 can be seen. Further, the extent L2 of the respective lateral seam or the lateral seam region 14 in longitudinal direction 9 can be seen, which also corresponds to the length of the respective longitudinal border section 10 at 12. According to the invention, the ratio L2/L1 is at least 0.42.

Further, the distance L4 of the outermost waist-facing first elastifying means 28, 29 in longitudinal direction 9 to the innermost crotch-facing first elastifying means 28, 29 can be seen. According to the invention, the ratio L4/L1 is at most 0.3.

It can further be seen, that the first elastifying means 28, 29 have a distance d1 to one another, which is at least 20% greater than the distance of the second elastifying means 40, 42 to one another defined in the lateral seam region 14. In the preferred shown case, the first elastifying means 28, 29 all have the same distance d1 to one another, which is at least 10 mm, in particular 10 to 15 mm. The ratio d1/L4 is preferably 0.08 to 0.25.

Further, L3 can be seen as the extent of the stomach section 4 and back section 6 in longitudinal direction 9, which for the stomach section 4 is in particular 135-260 mm and for the back section 6 in particular 200-320 mm.

Further shown is the extent Q of the stomach section 4 or the back section 6 in transverse direction 16, which enters into ratios L2/Q or L4/Q.

The first elastifying means 28, 29 have a thread strength, which is at least 20% greater than the thread strength of the second elastifying means 40, 42. In addition, the first elastifying means 28, 29 are fixed with a pre-tension with the chassis material layers in the stomach section 4 and in the back section 6, which pretension is 10% greater than that of the second elastifying means.

Reference is made to the further preferred afore described measurements, dimensions and ratios.

Figure 8:
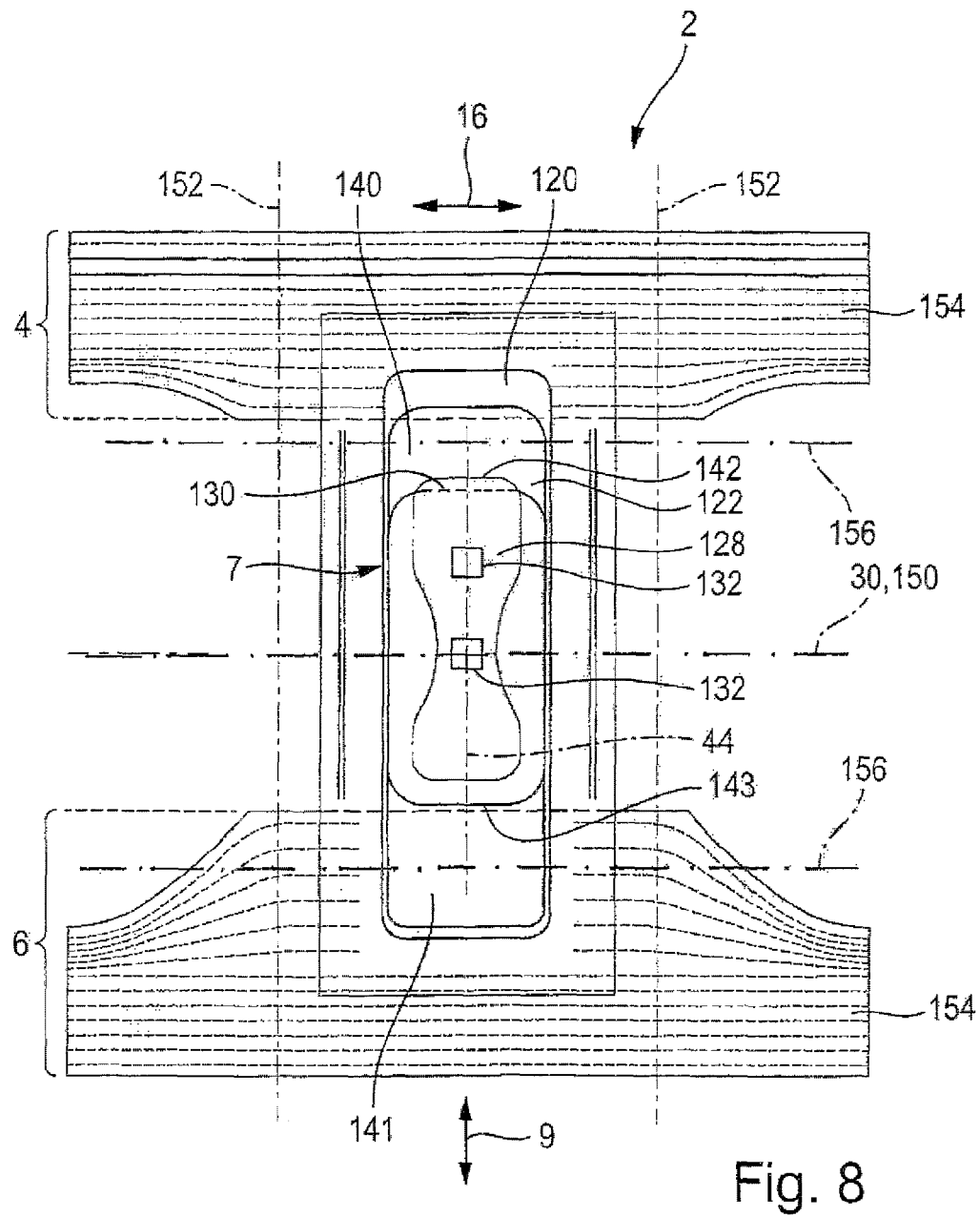
FIG. 8 shows a representation corresponding to FIG. 1, illustrating the construction of the absorption body and the folding axes.
Figure 9:
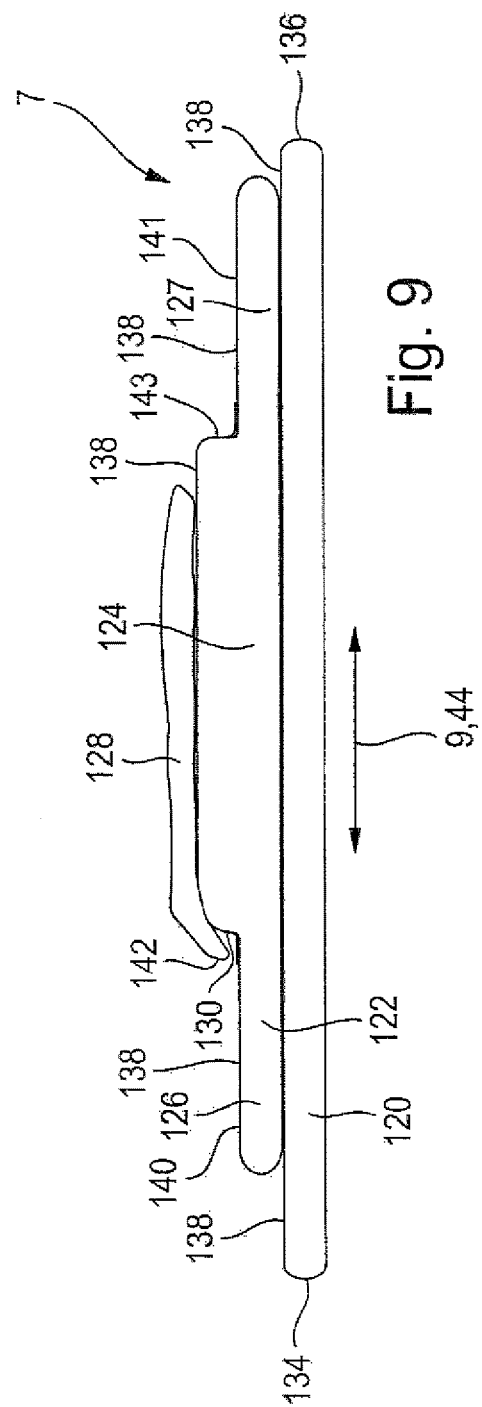
FIG. 9 shows a schematic longitudinal sectional view of the absorption body taken along the longitudinal center axis.

FIGS. 8 and 9 show the construction of the absorption body 7 in a top view and in a sectional view along the longitudinal center axis 44. Starting from its body-averted side, the absorption body 7 includes a basic layer 120 made of cellulosic fiber material with an exemplary mass per area of 176 g/m$^2$. Depending on the exact two-dimensional extent, the basic layer contains 10 to 14 g of cellulosic fiber material.

On the basic layer 120, a absorption body layer 122 is placed, which is three-dimensionally shaped at least with regard to the mass per area of absorption body material. In a center region 124, the absorption body layer 122 has a higher mass per area of absorption body material then in front and rear regions 126, 127, in longitudinal direction 9. In the exemplary shown case, the mass per area of cellulosic fiber material in the front and rear region 126, 127 of the absorption body layer 122 is 162 g/m$^2$ and in the center region 124 329 g/m$^2$. In addition, the absorption body layer 122 includes overall about 7 g of superabsorbent polymer materials, which are homogenously, evenly distributed in the absorption body layer 122. The regions 126, 127 and 124 are offset backward in longitudinal direction 9 relative to the two-dimensional extent of the basic layer 120 as can be seen from FIG. 8.

Finally, the absorption body 7 includes a body-facing liquid-absorption and distribution layer 128, which in the exemplary and preferred shown case has an hour class-shape, and predominantly extends on the center region 124 of the absorption body layer 122. The liquid-absorption and distribution layer 128 protrudes over a stomach-section-side longitudinal end 130 of the center region 124 of the absorption body layer 122. It includes a mass per area of fiber material i.e., in the form of intra-cross-linked cellulose fibers (curled fiber) of for example 149 g/m$^2$ with an overall mass corresponding to the exemplary extent of about 2.8 g.

The basic layer 120, the three regions 124, 126 and 127 of the absorption body layer 122 and the body-facing liquid absorption- and distribution layer 128 have a uniform mass per area of absorption body materials across their two-dimensional extent.

The mass per area is measured as described above by analyzing a test specimen of 25 mm×25 mm, which is punched out through all previously described layers of the absorption body 7. The area 132 (25 mm×25 mm) to be punched out is always centered relative to the longitudinal center axis 44, as indicated in FIG. 8. When the mass per area in longitudinal direction 9 is determined more frontward or more rearward, the test specimen is accordingly centered relative to the longitudinal center axis 44.

It can be seen that the mass per area of absorption body material thus decreases stepwise in the direction toward a stomach-section-side end 134 and in the direction toward a back-section-side end 136 of the absorption body 7. In this way, plateaus 138 are formed between the steps. In the region of these plateaus 138, the mass per area of absorption body material of the layers of the absorption body 7 lying there underneath is preferably but not necessarily, constant.

In the shown preferred embodiment of the incontinence article, the mass per area of the absorption body 7, starting from the transverse center axis 30 anteriorly and posteriorly in the region of the overlap of the body-facing liquid absorption- and distribution layer 128 with the center region 124 of the absorption body layer 122, is essentially constant.

In FIGS. 8 and 9, plateaus 140, 141 can be seen which adjoin a step 142, 143 anteriorly or posteriorly in the longitudinal direction 9. In the region of these plateaus 140, 141, the mass per area of the absorption body 7 is significantly reduced relative to the mass per area in the region of the transverse center axis 30.

Figure 10A:
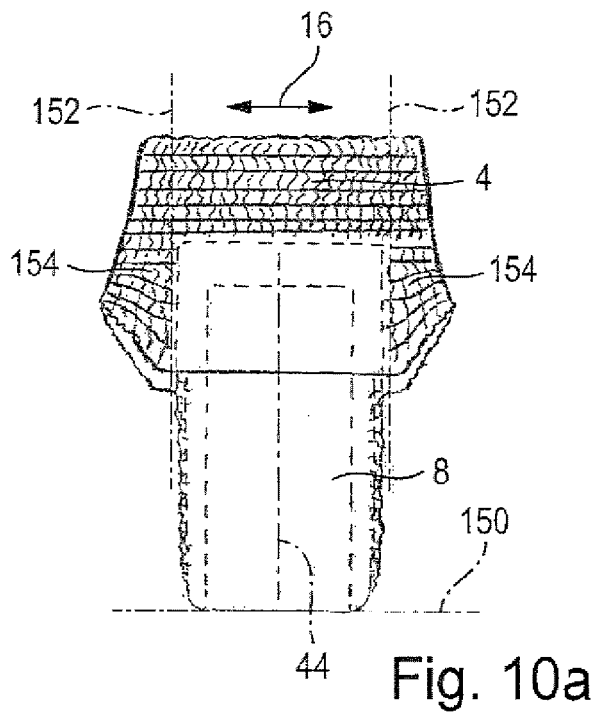
FIGS. 10 a,b,c show three schematic views of the incontinence article, illustrating the folding.

In the following, the folding of the incontinence article in pant form for the stacked arrangement of multiple incontinence articles in a packaging for distribution is described by way of the FIGS. 8, 10 and 11: as already mentioned, the transverse center axis 30 forms a first folding axis 150, about which the incontinence article is folded, so that the stomach section 4 and back section 6 can be permanently joined together for forming lateral seam regions 14 i.e., by conventional joining methods, such as gluing, ultrasound etc. Further, second folding lines 152 which approximately extend in longitudinal direction 9 are only outlined in FIG. 8, because the folding does not occur in the stretched out state shown in FIG. 8, but after finishing the pant-shaped incontinence article in the only schematically shown state in FIG. 10a. Starting from this outlined state shown in FIG. 10a, regions 154 of the stomach section 4 and back section 6 which laterally extend over the crotch section 8 on both sides, are folded in the direction towards the longitudinal center axis 44, preferably onto the outsides of the stomach section 4, so that the configuration outlined in FIG. 10 b is obtained.

Figure 10B:
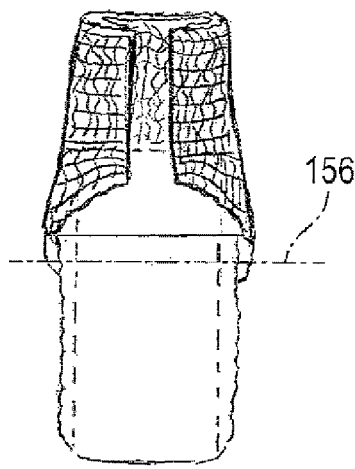
Figure 10C:
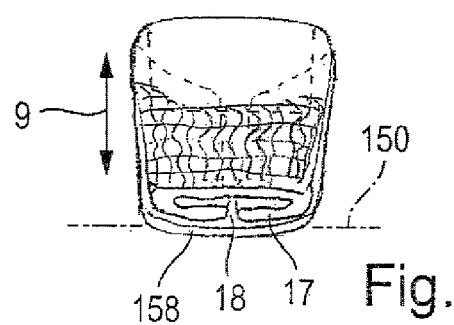

FIGS. 8 and 10 show a third folding axis 156, which extends in transverse direction 16, and whose position relative to the absorption body 7 can be seen from FIG. 8. Further folding about this only further folding axis 156, which extends in transverse direction 16, results in the compactly folded configuration of the pant-shaped incontinence article shown in FIG. 10c. It can be seen that the border of the stomach and back band 17, which delimits the waist opening 18, does not protrude in longitudinal direction 9 over the outer folding edge 158 of the incontinence article, which folding edge 158 is formed by the first folding axis 150.

Figure 11:
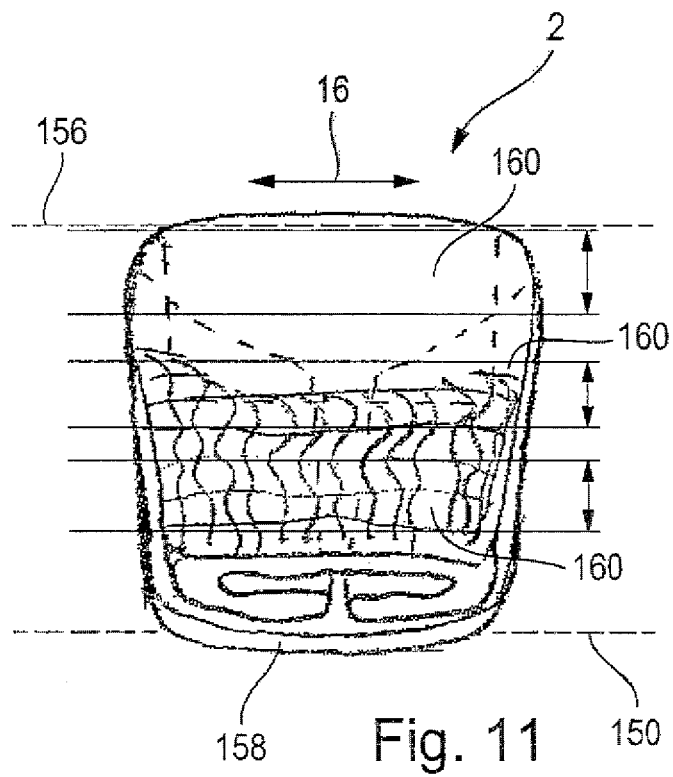
FIG. 11 shows a schematic view of the folded incontinence article, illustrating sampling during determination of the thickness.

FIG. 11 illustrates at which sites the thickness of the incontinence article 2, which is folded into the configuration of FIG. 10c, is determined. As already mentioned, the entire such folded incontinence article 2 is punched out over the entire transverse direction 16 with a punching knife at a distance of about 10 mm to the folding edges or folding axes 150 and 156, thereby forming strip-shaped test specimens 160. Based on these test specimens 160, which include all layers of the incontinence article, the thickness is then determined as described above.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

1. An incontinence article in pant form for absorbing bodily excretions, comprising:
   a stomach section;
   a back section, spaced apart from the stomach section in a longitudinal direction of the incontinence article along a longitudinal center axis, said stomach section and back section having respective lateral seam regions and being joined at the respective lateral seam regions thereby forming a stomach-and back band which is continuous in a transverse direction of the incontinence article, and has a circumferentially closed waist opening;
   a crotch section having an absorption body and extending in the longitudinal direction between the stomach section and the back section, said crotch section overlapping with the stomach section and the back section in respective overlapping regions and being non-detachably connected to the stomach section and to the back section in the respective overlapping regions, said stomach section, back section and crotch section together delimiting leg openings of the incontinence article, said stomach and back section having respective crotch-side regions facing the leg openings;

first elastifying means extending in spaced apart and parallel relationship to one another in the transverse direction in the stomach section and back section, thereby two-dimensionally elastifying the stomach section and the back section; and second elastifying means extending in the respective crotch-side regions of the stomach and back sections, in particular from the respective lateral seam regions towards the longitudinal center axis into the respective overlapping regions of the crotch section and back section and of the crotch section and stomach section, wherein the crotch section is non-detachably connected to the stomach section and to the back section with plural adhesive strips provided in the respective overlapping regions, said plural adhesive strips extending in parallel relationship to one another in the transverse direction of the incontinence article and are separated from each other by adhesive-free strips, thereby forming visually and/or tactilely perceivable structures on an outer visible side of the incontinence article in the respective overlapping regions, wherein a course of said structures corresponds to a course of the adhesive strips and the adhesive-free strips, wherein respective wider ones of the adhesive strips are respectively provided in a waist-proximal border region and/or a waist-distal border region of the respective overlapping regions, said waist-proximal border region or said waist-distal border region occupying at most 20% of an extent of the respective overlapping regions in the longitudinal direction.

2. The incontinence article of claim 1, wherein a width of the adhesive strips transverse to their extent in the transverse direction is at least 1 mm to at most 5 mm.

3. The incontinence article of claim 1, wherein a width of the adhesive-free strips transverse to their extent in the transverse direction is at least 1 mm to at most 15 mm.

4. The incontinence article of claim 1, wherein a width of the wider adhesive strips transverse to their extend is at least 5 mm, to at most 14 mm.

5. The incontinence article of claim 1, wherein a ratio between a width of the adhesive strips to a width of immediately neighboring ones of the adhesive-free strips is 0.2-3.0.

6. The incontinence article of claim 1, wherein a width at least of those of the adhesive strips that are positioned inwardly relative to optionally provided border-side adhesive strips are of a same size.

7. The incontinence article of claim 1, wherein the adhesive-free strips are defined by a same width.

8. The incontinence article of claim 1, wherein a total surface of the adhesive strips is 35%-60% of one of the respective overlapping regions.

9. The incontinence article of claim 1, wherein a mass per area of a glue coating in the adhesive strips is 2-20 g/m2, and wherein the mass per area in all adhesive strips is preferably the same.

10. The incontinence article of claim 1, wherein a surface of the overlapping region of crotch section and stomach section is at least 12% of a surface of the stomach section.

11. The incontinence article of claim 1, wherein a surface of the overlapping region of crotch section and back section is at least 20% of a surface of the back section.

12. The incontinence article of claim 1, wherein in the overlapping region of stomach section and crotch section at least 8 adhesive strips are provided and in the overlapping region of back section and crotch section at least 15 adhesive strips are provided.

13. The incontinence article of claim 1, wherein the second elastifying means fan out arch-shaped with increasing distance to one another along their extent in the direction toward the longitudinal center axis of the incontinence article.

14. The incontinence article of claim 1, wherein the first and/or the second elastifying means in the respective overlapping regions extend parallel to the adhesive strips.

15. An incontinence article in pant form for absorbing bodily excretions, comprising:

a stomach section;

a back section, spaced apart from the stomach section in a longitudinal direction of the incontinence article along a longitudinal center axis, said stomach section and back section having respective lateral seam regions and being joined at the respective lateral seam regions thereby forming a stomach-and back band which is continuous in a transverse direction of the incontinence article, and has a circumferentially closed waist opening;

a crotch section having an absorption body and extending in the longitudinal direction between the stomach section and the back section, said crotch section overlapping with the stomach section and the back section in respective overlapping regions and being non-detachably connected to the stomach section and to the back section in the respective overlapping regions, said stomach section, back section and crotch section together delimiting leg openings of the incontinence article, said stomach and back section having respective crotch-side regions facing the leg openings;

first elastifying means extending in spaced apart and parallel relationship to one another in the transverse direction in the stomach section and back section, thereby two-dimensionally elastifying the stomach section and the back section; and second elastifying means extending in the respective crotch-side regions of the stomach and back sections, in particular from the respective lateral seam regions towards the longitudinal center axis into the respective overlapping regions of the crotch section and back section and of the crotch section and stomach section, wherein the crotch section is non-detachably connected to the stomach section and to the back section with plural adhesive strips provided in the respective overlapping regions, said plural adhesive strips extending in parallel relationship to one another in the transverse direction of the incontinence article and are separated from each other by adhesive-free strips, thereby forming visually and/or tactilely perceivable structures on an outer visible side of the incontinence article in the respective overlapping regions, wherein a course of said structures corresponds to a course of the adhesive strips and the adhesive-free strips, wherein in one or both of the respective overlapping regions two outer border-side adhesive strips are provided, and in longitudinal direction between the two outer border-side adhesive strips, plural inwardly located adhesive strips are provided, wherein a width of the border-side adhesive strips is greater than the width of the inwardly located adhesive strips.

16. The incontinence article of claim 15, wherein a width at least of those of the adhesive strips that are positioned inwardly relative to optionally provided border-side adhesive strips are of a same size.

17. The incontinence article of claim 15, wherein the adhesive-free strips are defined by a same width.

18. The incontinence article of claim 15, wherein a total surface of the adhesive strips is 35%-60% of one of the respective overlapping regions.

19. The incontinence article of claim 15, wherein in the overlapping region of stomach section and crotch section at least 8 adhesive strips are provided and in the overlapping region of back section and crotch section at least 15 adhesive strips are provided.

\* \* \* \* \*